US00PP31940P2

(12) United States Plant Patent
Malinowski et al.

(10) Patent No.: US PP31,940 P2
(45) Date of Patent: Jul. 7, 2020

(54) ***HIBISCUS* PLANT NAMED '15714-1N'**

(50) Latin Name: ***Hibiscus* hybrid (L.)**
Varietal Denomination: 15714-1N

(71) Applicant: The Texas A&M University System, College Station, TX (US)

(72) Inventors: Dariusz P. Malinowski, Vernon, TX (US); William E. Pinchak, Vernon, TX (US); R. Steve Brown, Vernon, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 16/501,698

(22) Filed: May 22, 2019

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 5/02
See application file for complete search history.

(56) References Cited

PUBLICATIONS

U.S. Appl. No. 16/501,691, filed May 22, 2019, Malinowski et al.
U.S. Appl. No. 16/501,696, filed May 22, 2019, Malinowski et al.
U.S. Appl. No. 16/501,694, filed May 22, 2019, Malinowski et al.
U.S. Appl. No. 16/501,693, filed May 22, 2019, Malinowski et al.
U.S. Appl. No. 16/501,695, filed May 22, 2019, Malinowski et al.
U.S. Appl. No. 16/501,692, filed May 22, 2019, Malinowski et al.
U.S. Appl. No. 16/501,697, filed May 22, 2019, Malinowski et al.

*Primary Examiner* — Keith O. Robinson
(74) *Attorney, Agent, or Firm* — Dentons US LLP

(57) ABSTRACT

'15714-1N' is a new and distinct hardy herbaceous *Hibiscus* hybrid with novel characteristics that include upright branched stems, numerous, outward-facing, very light purplish-blue flowers, which can intensify in response to high UV radiation, and a center eye that is between dark red (RHS 59A) and deep purplish red (RHS 59B), with the outer part of the eye moderate red (RHS 185B), a prolonged blooming season, and hastate, trilobed leaves.

4 Drawing Sheets

Latin name of the genus and species of the plant claimed: *Hibiscus* hybrid (L.).

Cultivar denomination: '15714-1N'.

BACKGROUND OF THE INVENTION

The invention relates to the new and distinct *Hibiscus* plant '15714-1N'. '15714-1N' was generated from a cross performed on Jul. 22, 2014 near Vernon, Tex. between '12078-5' (pod parent, unpatented) and '13099-6' (pollen parent, unpatented). The pedigrees of each parent reflect a complex mixture of *Hibiscus* species that include, for example, *H. mocheutos, H. coccineus, H. militaris,* or *H. dasycalyx*. The seed from this cross was harvested on Aug. 31, 2014 and the '15714-1N' seedling was selected in the summer of 2015. '15714-1N' was first asexually propagated near Vernon, Tex. in 2016 by stem tip cuttings. The resulting as well as subsequent asexually propagated plants have been stable and true to type throughout successive generations.

SUMMARY OF THE INVENTION

'15714-1N' differs from its parents and all other known hardy herbaceous *Hibiscus* plants. The following are the most outstanding and distinguishing characteristics of '15714-1N': (1) it is a hardy perennial with dense branching and a compact growth habit; (2) it blooms profusely over a prolonged season; and (3) its flowers exhibit very light purplish-blue (RHS 100C) background, which can intensify in response to high UV radiation, and a center eye that is between dark red (RHS 59A) and deep purplish red (RHS 59B), with the outer part of the eye moderate red (RHS 185B).

'15714-1N' plants can be readily and unambiguously distinguished from those of its parents. '15714-1N' plants exhibit very light purplish-blue (RHS 100C) flowers that have an average diameter of 12 cm and hastate, trilobed leaves. Whereas, '12078-5' plants (pod parent) exhibit light purplish blue (RHS95D) to very pale purplish blue (RHS 97C) flowers that have an average diameter of 10 cm and lobed leaves; and '13099-6' plants (pollen parent) exhibit very pale purple (RHS 97D) to light blue (RHS 108D) flowers that have an average diameter of 15 cm and hastate leaves.

'15719 GRW' (U.S. patent application Ser. No. 16/501,696) is the *Hibiscus* plant that exhibits flowers that are colored most similarly to those of '15714-1N'. Nonetheless, plants of '15714-1N' and '15719 GRW' can also be readily and unambiguously distinguished from one another at least based upon flower shape, petal shape, and growth habit. The petals of '15714-1N' are cupped and overlap; whereas the petals of '15719 GRW' are not cupped or overlapping. Also, plants of '15714-1N' display a growth habit that is more compact than plants of '15719 GRW'.

BRIEF DESCRIPTION OF THE DRAWINGS

'15714-1N' is illustrated by the accompanying photographs, which show the plant's form, foliage, flowers, and leaves. The colors shown are as true as can be reasonably obtained by conventional photographic procedures.

DETAILED BOTANICAL DESCRIPTION

Figure 1:
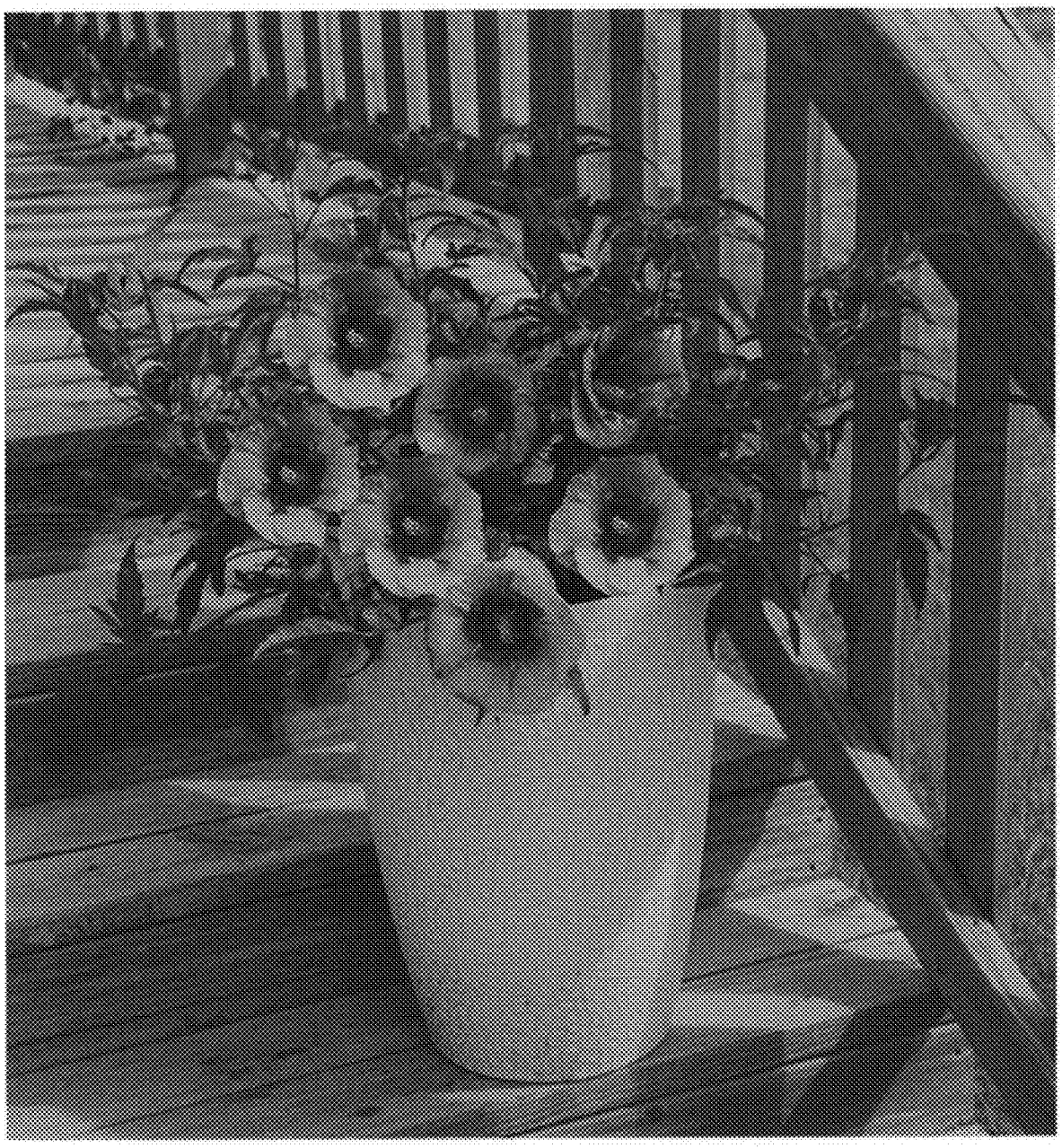
FIG. 1—Shows a 6-week-old '15714-1N' plant in a container.
Figure 2:
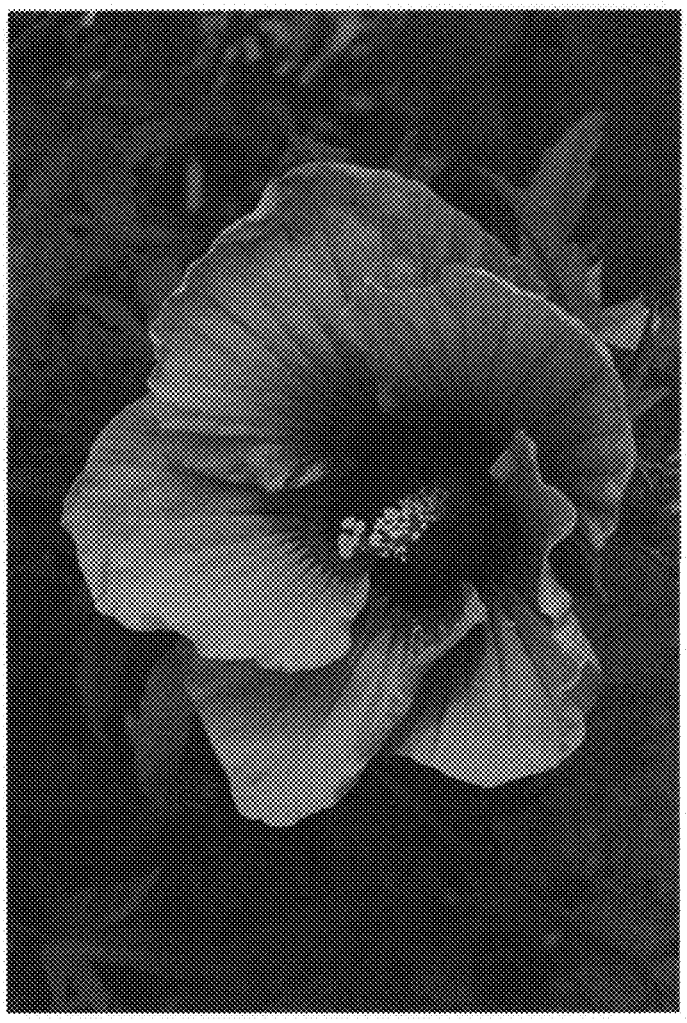
FIG. 2—Shows a '15714-1N' flower as seen looking slightly askew from the adaxial surface of the petals on a 2-year-old plant.
Figure 3:
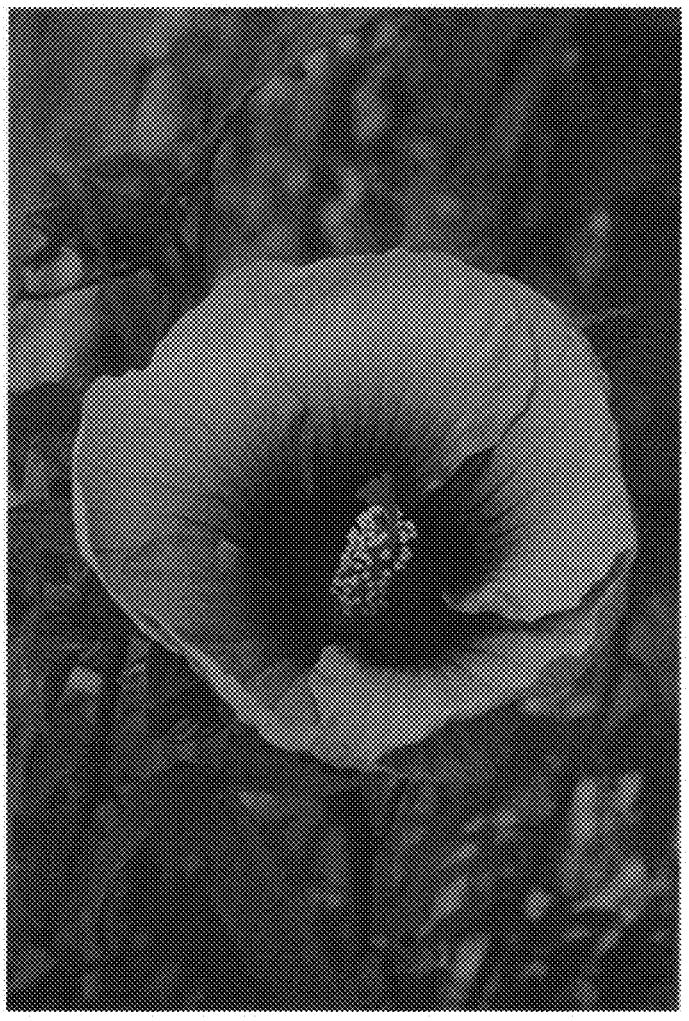
FIG. 3—Shows a '15714-1N' flower as seen looking slightly askew from the adaxial surface of the petals on a 2-year old plant.
Figure 4:
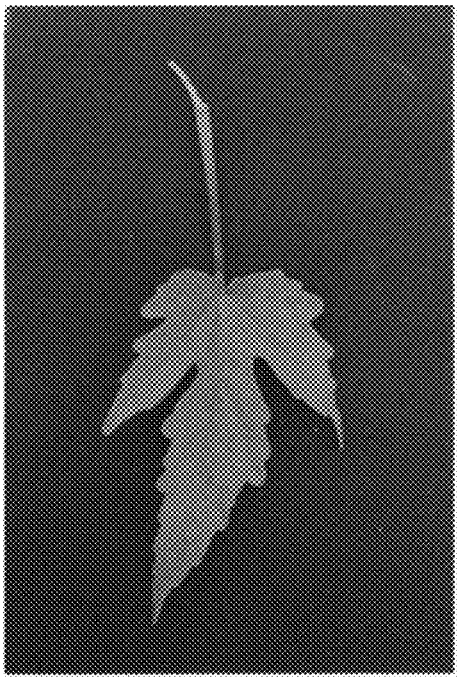
FIG. 4—Shows a '15714-1N' leaf.

The following detailed description sets forth the distinctive characteristics of '15714-1N'. The detailed description was obtained using two-year-old plants grown in loamy sand, open-field, full sun trials at a nursery near Vernon, Tex., during which the plants were supplemented with fertilizer and water as needed. These plants are natural habit and were not treated with plant growth regulators and they were not pinched at any time in the growth year. '15714-1N' has not been observed under all possible environments, and certain characteristics may vary slightly under different environmental conditions. Color references are to The Royal Horticultural Society Colour Chart of The Royal Horticultural Society of London (R.H.S.), 2001 ($4^{th}$ edition).

Propagation:

*Method.*—Stem cuttings.

*Time to initiate roots from stem cuttings after treating cuttings with a commercial rooting hormone.*—About 2 weeks under misting and at an air temperature of 85° C.

*Rooting habit.*—Normal, branching, fleshy, and developing a thick diameter (to about 2.5 cm).

*Root color.*—Pale yellow (between RHS 161D and RHS 162D), depending on soil type.

*Crop time (under normal summer growing conditions and when grown in a 4 L container from a rooted cutting).*—8 to 10 weeks to flower with very good plant vigor.

Plant:

*Plant shape and habit.*—Hardy herbaceous perennial with 8 to 10 thick upright and branched main stems producing an upright spreading mound about 70 cm tall and 70 cm wide, which is widest about 30 cm above the soil line.

*Primary branches.*—8 to 12 per main stem that protrude at about a 75° angle from horizontal.

*Lateral branches.*—On the middle half of the primary stems.

*Lateral branch size.*—Between 15 cm and 35 cm long (shorter at the upper nodes) and with an average diameter of 8.0 mm at their base.

*Flower location.*—Upper ⅓ of the plant beginning at axillary nodes while still developing at the apex.

*Stem.*—Rounded, glabrous, glaucous; averages about 70 cm tall and 3.5 cm diameter at their base.

*Stem color.*—Between dark red (RHS 187B) and dark red (RHS 187C).

*Internode.*—About 18 nodes per stem below flower and about 28 total, average internode length is about 4.5 cm of unpinched plant, but varies between 2.0 to 6.0 cm and are longest in middle portion of stem.

Foliage:

*Shape.*—Hastate, trilobed with slightly indented margins.

*Texture.*—Adaxial and abaxial matte.

*Leaf blade size.*—To about 15.0 cm long and 7.5 cm wide, larger proximally and becoming smaller in distal portion of stem.

*Foliage color.*—Adaxial and abaxial moderate green (RHS 135B).

*Veins.*—Palmate; adaxial and abaxial veins moderate yellowish green (RHS 138C).

*Petioles size (average).*—7.0 cm long and 5.0 mm wide.

*Petiole color.*—Between dark red (RHS 187B) and dark red (RHS 187C).

Flowers:

*Buds.*—One day prior to opening, about 3.5 cm long and 2.5 cm in diameter, pointed apex and bluntly rounded base, unopened petals wrinkled at veins; and, prior to showing petals, about 3.5 cm long and 2.5 cm in diameter, ovoid with acute apex.

*Bud color.*—Exposed petal light violet (RHS 93D) toward apex with vein tinting of strong violet (RHS 93C); and, prior to showing petals, light violet (RHS 93D).

*Epicalyx.*—Entire, smooth, puberulent both surfaces, linear with sharply acute apex and attenuate base, curved around sepals; typically 10 to 12 per flower; about 2.5 cm long tapering to base of about 3.0 mm wide.

*Epicalyx color.*—Adaxial and abaxial strong yellowish green (RHS 135C).

*Sepals.*—5, proximal half connate forming campanulate star-shaped calyx; acute apex; margin entire, edentate; puberulent abaxial glabrous adaxial; individually about 3.5 cm long and about 2.5 cm wide at fusion point. From the upper side of the flower, sepals visible as a star shape in the center of the flower.

*Sepal color.*—Abaxial color strong yellowish green (RHS 135C), sepal edge color dark red (RHS 183B); adaxial color strong yellowish green (RHS 135C).

*Flowers.*—Solitary, about 15 to 25 per main stem without pinching; primarily outwardly facing; average 12 cm across; persist for one to two days, depending on temperature; effective for at least 14 weeks beginning early July and lasting into October (north Texas), no detectable fragrance.

*Petals.*—5; glabrous, dull both front and back, adnate to the androecium to form a column, slightly imbricate to about 35% overlapping at widest part (petals about 70% overlapping the next petal to either side). Veins: Parallel individual veins impressed on front and ribbed on back; veins extend from the eye zone; strong purplish red (RHS 61B). Shape: Rounded. Margins: Entire, edentate, frilled. Apex: Rounded. Base: Short claw-like. Surface: Adaxial and abaxial glabrous, slightly ribbed. Size (average): About 11.0 cm long and about 10.0 cm wide at widest portion (largest in earlier part of flowering season); center dark eye about 5.0 cm diameter. Color: Adaxial and abaxial very light purplish blue (RHS 100C), center eye between dark red (RHS 59A) and deep purplish red (RHS 59B), outer part of the eye moderate red (RHS 185B).

*Gynoecium*.—Style: Enclosed in column about 5 cm long and 0.5 cm wide at base; column color deep purplish red (RHS 61D); style protruding from column and split in distal 10.0 mm portion into typically 5 branches, branch diameter 2.0 mm; branch color nearest deep purplish red (RHS 61D). Stigma: Typically 5; globose, puberulose, about 3.0 mm in diameter; color nearest pale purplish pink (RHS 62D). Ovary: Superior, about 6.5 mm across at base and 6.0 mm tall; acute apex.

*Androecium*.—Filaments: Numerous, about 140; less than 1.0 mm in diameter and about 5.0 mm long; attached along nearly the entire length of column; color nearest pale purplish pink (RHS 62D). Anthers: Reniform; about 2 mm long and 1 mm wide; nearest light yellow (RHS 163D). Pollen: Numerous, globose, less than 0.1 mm long; color light yellow (RHS 163D).

*Pedicel*.—Rounded in cross section, smooth; length from base of sepal to abscission point average 1.5 cm long and 4.0 mm wide, longer on early flowers decreasing in later flowers; color brilliant yellowish green (RHS 135C).

*Peduncle*.—Rounded, puberulent, average about 2.5 cm long from abscission point to stem and 4.0 mm wide, slightly longer on earlier flowers.

*Peduncle color*.—Brilliant yellowish green (RHS 135C) with slight tint between dark red (RHS 187B) and dark red (RHS 187C).

*Fruit*.—Few, loculicidal capsule; glabrous; globose, occasionally with abruptly acute apex; color between light yellowish brown (RHS 199C) and dark grayish yellow (RHS 199D) when mature.

*Seed*.—Minutely floccose, typically globose; about 3.0 mm in diameter; color between dark grayish reddish brown (RHS 200A) and moderate brown (RHS 200C).

Resistance: The plant grows best with plenty of moisture, but is able to tolerate some drought once established. Other pest and disease resistance beyond that of other hardy perennial *Hibiscus* cultivars has not been observed. Hardiness at least from USDA Zone 4 through 9.

Commercial use: Suitable for potted plant culture, landscaping as a specimen or en masse, and especially suited for patios and confined spaces because of the compact habit.

What is claimed is:

1. A new and distinct *Hibiscus* hybrid (L.) plant named '15714-1N' as shown and described herein.

* * * * *